United States Patent [19]

Bowman

[11] 4,365,635
[45] Dec. 28, 1982

[54] PRESSURE TRANSDUCING METHODS AND APPARATUS

[75] Inventor: Ronald Bowman, Laguna Beach, Calif.

[73] Assignee: Bell & Howell Company, Chicago, Ill.

[21] Appl. No.: 239,921

[22] Filed: Mar. 3, 1981

[51] Int. Cl.³ .............................................. A61M 5/00
[52] U.S. Cl. ................................ 128/675; 128/214 F; 55/204; 141/322
[58] Field of Search ............... 128/214, 214 E, 214 F, 128/DIG. 12, DIG. 13, 675; 55/204, 205; 141/18, 29, 110, 322, 311

[56] References Cited

U.S. PATENT DOCUMENTS

| | | | |
|---|---|---|---|
| 2,779,503 | 1/1957 | Wright et al. | 55/205 X |
| 3,157,201 | 11/1964 | Littman | 137/625.47 |
| 3,351,105 | 11/1967 | Di Perna | 141/18 |
| 3,565,056 | 2/1971 | Statham | 128/2 |
| 3,623,479 | 11/1971 | Day | 128/2.06 E |
| 3,631,850 | 1/1972 | Levasseur | 128/2.05 D |
| 3,730,186 | 5/1973 | Edmunds et al. | 128/325 |
| 3,731,680 | 5/1973 | Wright et al. | 128/214 E |
| 3,807,142 | 4/1974 | Rich et al. | 55/191 |
| 3,811,429 | 5/1974 | Fletcher et al. | 128/2.05 E |
| 3,865,100 | 2/1975 | Kanai et al. | 128/2.05 E |
| 3,942,564 | 3/1976 | Nakazato | 141/348 |
| 3,996,027 | 12/1976 | Schnell et al. | 55/36 |
| 4,063,553 | 12/1977 | Karsh | 128/214 F |
| 4,063,555 | 12/1977 | Ulinder | 128/214 |
| 4,070,168 | 1/1978 | Beattie | 55/205 |

OTHER PUBLICATIONS

*Health Devices,* Disposable Diaphragm Domes, Jul. 1979, pp. 206-207.

*Primary Examiner*—Stephen C. Pellegrino
*Attorney, Agent, or Firm*—Benoit Law Corporation

[57] ABSTRACT

Methods and apparatus for handling a compatible solution relative to a circulatory system of a living organism employ a recipient device having a circular cavity tending to retain gas bubbles. A pocket communicating with an opening for injecting the compatible solution is provided in the circular cavity. A unidirectional jet of the injected solution is formed by blocking flow of the injected solution at a closed end of the pocket, thereby forming a pressure head in the pocket. The injected solution is then ejected through an outlet of the pocket and is swept in a swirling motion along a boundary of the cavity, thereby wiping gas bubbles from such boundary, for bleeding to atmosphere.

25 Claims, 3 Drawing Figures

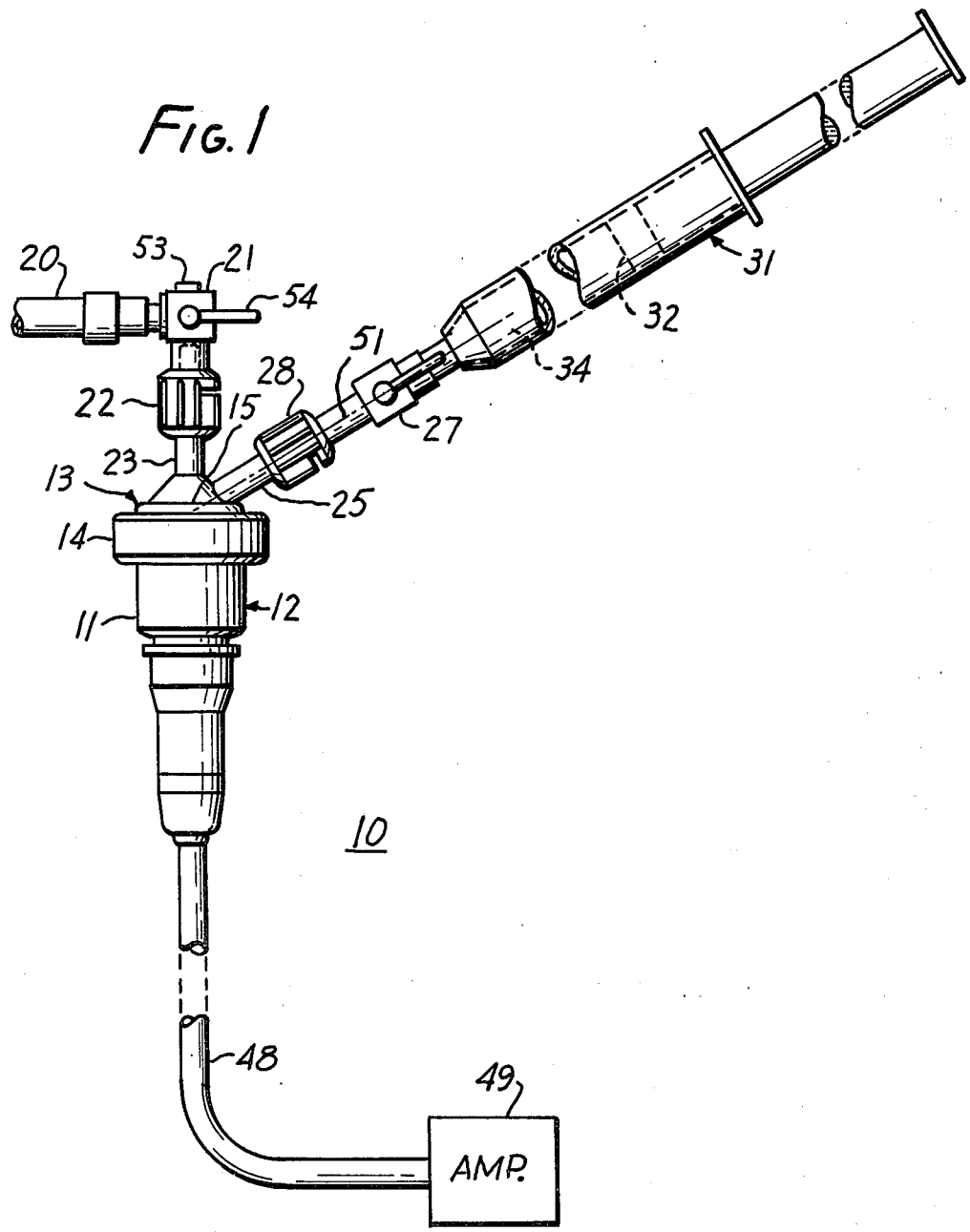

U.S. Patent    Dec. 28, 1982    Sheet 2 of 2    4,365,635
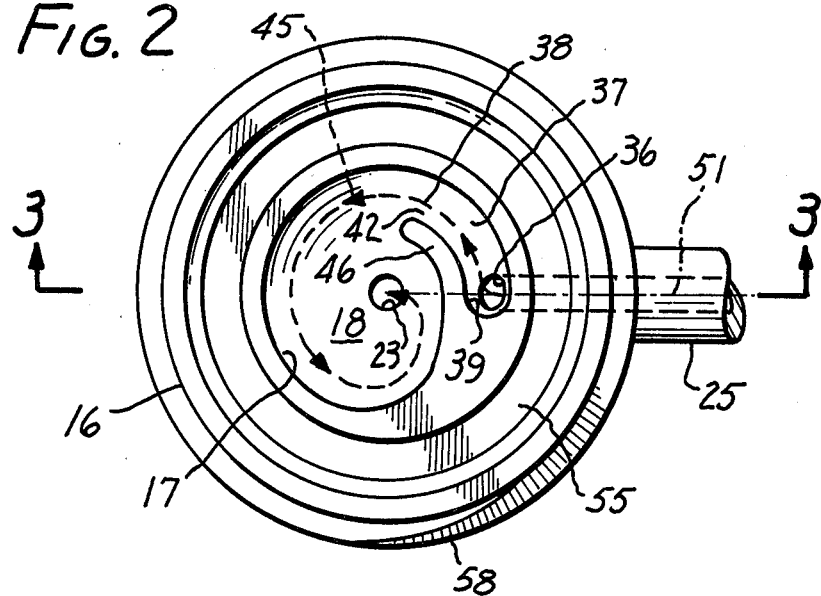
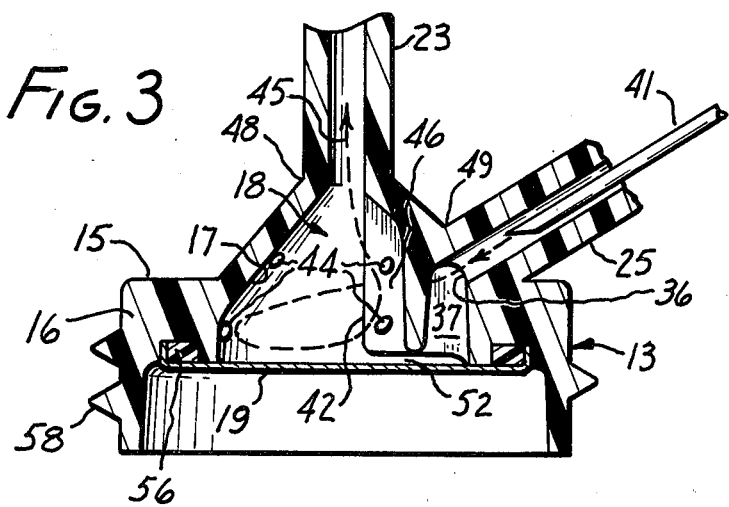

PRESSURE TRANSDUCING METHODS AND APPARATUS

BACKGROUND OF THE INVENTION

1. Field of the invention.

The subject invention relates to pressure transducers and to methods and apparatus for handling a compatible solution relative to the circulatory system of a living organism with the aid of a catheter.

2. Disclosure statement.

The following disclosure statement is made pursuant to the duty of disclosure imposed by law and formulated in 37 CFR 1.56(a). No representation is hereby made that information thus disclosed in fact constitutes prior art, inasmuch as 37 CFR 1.56(a) relies on a materiality concept which depends on uncertain and inevitably subjective elements of substantial likelihood and reasonableness, and inasmuch as a growing attitude appears to require citation of material which might lead to a discovery of pertinent material though not necessarily being of itself pertinent. Also, the following comments contain conclusions and observations which have only been drawn or become apparent after conception of the subject invention or which contrast the subject invention or its merits against the background of developments which may be subsequent in time or priority.

The design and operation of equipment for handling a compatible solution relative to the circulatory system of a living organism shares with the design and operation of liquid pressure transducing devices a concern over the removal of air bubbles from the compatible solution or other liquid. Reference may, in this respect, be had to pages 202 et seq. of HEALTH DEVICES (July, 1979) published by the Emergency Care Institute, of Plymouth Meeting, PA 19462. As that publication cautions, "Even the smallest air bubble can cause significant waveform distortion and result in incorrect systolic and diastolic values. Make sure all air bubbles are flushed from the catheter, tubing, stopcocks, and especially the transducer dome chamber."

In general, the compressible nature of air bubbles diminishes and otherwise degrades a pressure transducer signal, while injurious or fatal effects may result from an injection of air bubbles into living organisms.

Yet, because of surface tension and other effects, air bubbles at the boundaries of liquid-receiving cavities, tend to resist externally induced attempts at their removal.

In this respect and with regard to present and potential areas of utility of the subject invention, reference may, for instance, be had to U.S. Pat. No. 3,157,201, by D. Littmann, issued Nov. 17, 1964, for a fluid exchange valve between a glucose or saline solution reservoir, a catheter and a transducer, U.S. Pat. No. 3,351,105, by M. S. Di Perna, issued Nov. 7, 1967 for a rechargeable dispenser including a ball valve, U.S. Pat. No. 3,565,056, by L. D. Statham, issued Feb. 23, 1971, for a body fluid pressure measuring device connected to a saline solution supply and to a needle or catheter, U.S. Pat. No. 3,631,850, by J. E. Levasseur, issued Jan. 4, 1972, for a pressure transducer apparatus for microhemocirculation studies, including a pressure dome formed of a flat base having a diaphragm portion and sidewalls that converge into a central opening coupled to a microcannula, U.S. Pat. No. 3,730,186, by L. H. Edmunds et al., issued May 1, 1973, for an adjustable implantable artery-constricting device, U.S. Pat. No. 3,731,680, by F. A. Wright, issued May 8, 1973, for a pressure monitor and control device particularly useful in a method for effecting extra-corporeal hemodialysis, U.S. Pat. No. 3,807,142, by S. R. Rich, issued Apr. 30, 1974, for high efficiency removal of gases and particles from paper pulp suspensions and other fluids, employing vortical separation stages, U.S. Pat. No. 3,811,429, by J. C. Fletcher et al., for an arterial pulse wave pressure transducer having a flexible membrane adjacent a fluid-filled cavity adapted to be placed on the skin over an artery, U.S. Pat. No. 3,865,100, by H. Kanai et al., issued Feb. 11, 1975 for apparatus for measuring blood pressure, including a dumbbell-shaped damping device, U.S. Pat. No. 3,942,564, by T. Nakazato, issued Mar. 9, 1976, for a fuel tank filling inlet port device designed for selective acceptance of different diameter filling nozzles, U.S. Pat. No. 3,996,027, by W. J. Schnell et al., issued Dec. 7, 1976, for a swirling flow bubble trap in which liquid is passed for swirling flow within a chamber for a migration of gas bubbles from an inner wall towards the center of the swirling flow, and U.S. Pat. No. 4,063,555, by B. Ulinder, issued Dec. 20, 1977, for a cannula assembly designed for administration of fluids from two separate sources of supply, and including a check valve associated with one fluid inlet.

Reference may in this respect also be had to U.S. Pat. 3,623,479, by C. C. Day, issued Nov. 30, 1971, for ECG electrode having a partition for preventing hydrostatic locks through intrusion of skin into the dome-shaped electrode. According to an embodiment disclosed in that patent, the partition may be segmented to provide separate spaced contact areas with the skin to better restrain the skin from intruding the cavity and for directing the flow of an electrically conductive paste from an entrance hole, and the expurgation of entrapped air throughout the cavity to exit holes. Such partition segments have sharp corners to reduce flow resistance to the entrapped air and conductive paste and supposedly to better guide their flow. In practice, however, the latter proposal is pretty much restricted to its disclosed form of utility, since the curved partition segmentation in question compartmentalizes the available conductive paste flow into a plurality of parallel branches, thereby substantially reducing the attainable momentum with which air bubbles could be swept from cavity boundaries.

An attractive solution to the problem under consideration is apparent from U.S. Pat. No. 4,063,553, by H. Karsh, issued Dec. 20, 1977, to the subject assignee. According to the methods and apparatus disclosed in the latter patent, a compatible solution is injected into a circular liquid-receiving cavity in a whirl which sweeps all regions of the circular cavity, thereby vigorously removing gas bubbles therefrom.

The embodiment shown by way of example in the latter patent employs an inlet tube for injecting the compatible solution at a predetermined location in a direction extending at an angle to a diametrical plane through the circular cavity and that predetermined location. The particular inlet tube is thus laterally offset from the catheter tube on the transducer dome.

In practice, this complicates the manufacture of the transducer dome structure relative to an arrangement in which both tubes would extend in the same diametrical plane. Of course, this does not derogate from the utility of the latter solution, but it does render its implimentation potentially expensive and in need of special manufacturing steps.

For completeness' sake, reference may also be had to my U.S. Pat. No. 4,291,701, issued Sept. 29, 1981 to the common assignee, for pressure transducing and methods and apparatus for building a cavity, and assigned to the subject assignee. In that copending application, I disclose, for example, a single-port pressure transducer dome in which a liquid injection needle is partially inserted into a straight passage of the port and is stopped by engagement inside the port short of the liquid-receiving cavity, while an overflow and gas escape path is provided through the straight passage along the outside of the stopped, partially inserted needle. If desired, the teachings of the subject invention may also be applied to those and other single-port dome structures.

SUMMARY OF THE INVENTION

It is a general object of this invention to overcome the disadvantages and to meet the needs expressed or implicit in the above disclosure statement or in other parts hereof.

It is a related object of this invention to provide improved methods and apparatus for handling compatible solutions relative to circulatory systems of living organisms.

It is a germane object of this invention to provide improved methods and apparatus for keeping gas bubbles out of circulatory systems.

It is a related object of this invention to facilitate the removal of gas bubbles from liquid-containing cavities.

It is also an object of this invention to provide improved methods and apparatus for transducing pressure signals relative to liquids.

It is a related object of this invention to provide improved pressure transducers and parts therefor.

From one aspect thereof, the subject invention resides in a method of keeping gas bubbles out of a circulatory system of a living organism connected via a catheter insertible into the circulatory system to a recipient device having a circular cavity connected to such catheter and tending to retain gas bubbles. The invention according to this aspect resides, more specifically, in the improvement comprising, in combination, the steps of providing at the circular cavity an opening for injection of the compatible solution, providing in such circular cavity a pocket communicating with the mentioned opening, and injecting the compatible solution through the mentioned opening into the pocket in the circular cavity.

According to this aspect of the invention, a unidirectional jet of the injected solution is formed by blocking flow of the injected solution at a closed end of the pocket, thereby forming a pressure head in such pocket, and by ejecting the injected solution through an outlet of the pocket. The ejected solution is thus swept in a swirling motion along a boundary of the circular cavity, thereby wiping gas bubbles from such boundary, for a bleeding of gas from the wiped gas bubbles out of the circular cavity.

From another aspect thereof, the subject invention resides in apparatus for handling a compatible solution relative to a circulatory system of a living organism with the aid of a catheter insertible into the circulatory system. The invention according to this aspect resides, more specifically, in the improvement comprising, in combination, means for receiving the compatible solution having a circular cavity, means connected to such receiving means for coupling the catheter to the circular cavity, means connected to the receiving means for injecting the solution into the cavity through an opening, and means for imparting a swirling motion to the injected solution to wipe gas bubbles from a boundary of the cavity. The latter imparting means include and delimit a pocket in the circular cavity for forming a unidirectional jet of the injected solution. That pocket has a closed bottom at the solution injecting opening for blocking flow of the injected solution to form a pressure head in the pocket. Such pocket also has an outlet at the mentioned boundary for projecting the injected compatible solution into the circular cavity in the mentioned swirling motion, whereby to wipe gas bubbles from the boundary for a bleeding thereof from the circular cavity.

Other aspects and objects of the invention will become apparent in the further course of the disclosure, and no limitation to any particular method, apparatus, combination or component is intended by the subject summary of the invention.

BRIEF DESCRIPTION OF THE DRAWINGS

The subject invention and its various objects and aspects will become more readily apparent from the following detailed description of preferred embodiments thereof, illustrated by way of example in the accompanying drawings, in which like reference numerals designate like or functionally equivalent parts, and in which:

FIG. 1 is an elevation of part of a blood pressure transducing system embodying the subject invention;

FIG. 2 is a bottom view, on an enlarged scale, of a transducer dome employed in the system of FIG. 1; and FIG. 3 is a section taken on the line 3—3 in FIG. 2 and inverted so as to be oriented in the manner of FIG. 1.

DESCRIPTION OF PREFERRED EMBODIMENTS

The blood pressure transducing system 10 shown in the drawings has a blood pressure transducer 12 provided with a transparent dome 13 of glass or a suitable plastic. The dome 13 is threaded into a circular nut 14 on the transducer body 11. In the illustrated preferred embodiment, the part 13 has a flat top 15 for minimizing the solution or liquid volume at the transducer. However, the part 13 is still generally referred to as a "dome" and may in fact be dome-shaped.

A lateral flange 16 of the dome 13 defines part of a circular wall portion 17 of a cavity 18 inside the dome 13 between the top of the dome and the diaphragm of the pressure transducer located below the dome 13 or an auxiliary diaphragm 19 that may be placed across the bottom of the dome cavity 18 as shown in FIG. 3.

In practice, pressure signals are transferred to the cavity 18 from a living organism via a compatible solution in a catheter 20 which is connected to a shutoff valve 21. A Linden fitting 22 connects the valve 21 to a tube 23 attached to the dome 13 and issuing into the cavity 18 through its top. The tube 23 may be attached to the dome top at the center thereof, as shown, or then at a location spaced from the center, as desired.

The transducer 12 or dome 13 includes a second tube 25 which is attached to the dome 13 and issues into the cavity 18. A second shutoff valve 27 is attached to the tube 25 by a Linden fitting 28. Luer or other fittings may be employed instead.

A syringe 31 is attached to the valve 27 and communicates with the cavity 18 through the second tube 25 when the valve is open. The syringe 31 has a piston 32 for applying to the cavity 18 a solution that is physiologically compatible with the blood in the living organism to which the catheter 20 is connected in practice.

Depending on the condition of the living organism and the purpose to be accomplished, the compatible solution 34 in the syringe 31 may, for instance, be a saline or a dextrose solution.

In the operation of the equipment, the compatible solution 34 is injected with the syringe 31 through the second tube 25 into the circular cavity 18 and is rotated in that circular cavity in a whirl sweeping all regions of the circular cavity and having a peripheral portion encompassing a central axis of the circular cavity 18 and proceeding circumferentially along a peripheral boundary or circular wall portion 17.

In particular, the inlet tube 25 provides at the circular cavity 18 an opening 36 for injection of the compatible solution 34. The subject invention further provides in or at circular cavity 18 a pocket 37 communicating with the opening 36.

In other words, the means for imparting a swirling motion of the injected solution 34 to wipe gas bubbles from a boundary 17 of the cavity 18 include and delimit, according to the illustrated preferred embodiment of the subject invention, a pocket 37 in the cavity 18.

The illustrated preferred embodiment of the invention forms a unidirectional jet 38 of the injected solution by blocking flow of the injected solution at a closed end or bottom 39 of the pocket 37, thereby forming a pressure head in such pocket.

The illustrated preferred embodiment then completes formation of the unidirectional jet 38 with the aid of the compatible solution 34 injected through the inlet tube 25 or a hollow needle 41 of the syringe 31. In particular, the illustrated preferred embodiment thus ejects the injected solution through an outlet 42 of the pocket 37.

As seen in FIGS. 2 and 3, the pocket 37 is so oriented that the solution ejected therefrom is swept in a swirling motion along a boundary or wall of the cavity 18, thereby wiping gas bubbles 44 from such boundary or wall 17.

These gas bubbles are then bled out of the circular cavity through the top tube 23. The valve 21, typically structured as a three-way valve, may serve this purpose.

In order to avoid cluttering of the drawings, and because of the presence of reference numerals, a dotted line 45 indicates only a simple loop of the swirl generated in dome 13. In reality, the swirl 45 may, however, have several turns, sweeping the entire inside of the cavity, including the projection or sidewall 46 of the channel or pocket 37. The generated swirl 45 helps the ejection of gas bubbles by carrying them to the top outlet 23.

Further in accordance with the illustrated preferred embodiment, the catheter 20 is connected by the first tube 23 to the cavity 18 at a first predetermined location 48. The compatible solution 34 is injected into the cavity 18 through the second tube 25 at a second predetermined location 49 situated at a distance from and in the same diametrical plane 51 through the circular cavity 18 or dome 13 as the first tube 23.

In practice, this preferred arrangement considerably facilitates the manufacture of the dome arrangement, with tubes 23 and 25, as compared to designs in which either of the tubes would be laterally offset from a diametrical plane through the center of the dome and the other tube.

As seen in FIG. 2 and to some extent also in FIG. 3, the pocket 37 is curved along part of a boundary 17 of the circular cavity to increase the efficiency and effectiveness of the resulting liquid jet 38.

In the illustrated preferred embodiment, the pocket 37 is laterally delimited by a partition or director 46 joined to a wall 17 of the cavity 18 at the liquid injection opening 36, and extending in spaced relationship to such wall for part thereof. In this manner, the pocket 37 may be formed by providing in the cavity 18 a partition or director 46, being joined to the cavity wall 17 at the closed pocket bottom 39.

The latter partition 46 is preferably curved in the manner of the circular cavity 18, for optimum formation of the sweeping spiral liquid flow or whirl 45.

The duct provided by the inlet tube 25 and having the liquid injection opening 36 preferably extends at right angles to a periphery of the circular cavity, as seen in FIGS. 2 and 3, with the pocket 37 extending along part of such periphery or circular wall portion 17. This, in practice, enables manufacture of the dome 13 with a conventional mold, which favorably distinguishes the subject invention from prior-art approaches which required a rather complex multi-section mold in this respect.

Notwithstanding such simplification, the combination of the illustrated preferred embodiment still results in a sweeping liquid jet 38 which is angled relative to the inlet duct at 25, with a tangential trajectory at the liquid injection opening 36 of the dome.

In a similar vein, the illustrated preferred embodiment forms the pocket 37 as a canal having an open bottom, as seen in FIGS. 2 and 3. In this manner, the dome 13 may be manufactured by a simple molding or other straightforward manufacturing step. The illustrated preferred embodiment then at least partially closes the open bottom of the canal at 37, by suitable means covering such canal.

By way of example, the latter means may include a diaphragm 19 extending or being disposed across the circular cavity 18 and open bottom of the canal at 37.

In principle, the diaphragm 19 could be the diaphragm of a transducer. More advantageously, however, the diaphragm 19 may be an auxiliary diaphragm for closing the cavity 18 and, in the case of the illustrated preferred embodiment, also the pocket 37.

In this respect, the diaphragm 19 extends across the circular cavity 18 for deflection up to a maximum amplitude, such as in response to pressure variations in the system connected to the catheter 20. As seen in FIG. 3, the partition or director 46 is preferably spaced from the diaphragm 19 by a short distance 52 to avoid contact between such partition and the diaphragm during deflection at its maximum amplitude. By thus spacing the diaphragm 19 and partition 46 from each other, the illustrated preferred embodiment avoids an undesirable damping or similar undesirable effect due to the presence of the pocket 37 and partition 46.

In practice, the diaphragm 19 which thus forms a lateral part of the pocket 37, may be located in sufficient proximity to the partition 46 so as to preserve the principle of the illustrated preferred embodiment of providing the pocket 37 with a closed end or bottom 39 at the opening 36, for all practical intents and purposes.

The diaphragm 19 may advantageously convert the illustrated embodiment into a so-called "disposable diaphragm dome," having many practical advantages, including reduced risk of patient infection as compared to transducers and reusable domes, which may not always be properly sterilized. Reference may in this respect be had to the text on pages 206 and 207 of the above mentioned HEALTH DEVICES publication.

As indicated above, the whirl 45 sweeps all parts of the dome 13 and wipes air and other gas bubbles from the circular wall portion 17 and from other boundary surfaces including the dome 13 of the cavity before the moving solution reaches the tube 23. In practice, the removed gas bubbles may be bled to atmosphere through the tube 23 and an outlet 53 in the valve 21. To this end, the valve 21 is a three-way valve being manually actuable via a handle 54 between a first position in which the tube 23 is vented to atmosphere via outlet 53, with the catheter 20 being then blocked off from the cavity 18, and an alternative second position in which the outlet 53 is blocked off and the catheter 20 connected to the cavity 18.

The result of the above mentioned sweeping operation is an air and gas free solution or liquid-filled cavity 18 at which the transducer is mounted by means of the circular nut 14.

In practice, the injection of the compatible solution 32 through the tube 25 and cavity 18 is continued through the tube 23 and catheter 20 after the air bubbles have been removed as described above and the catheter has been connected to the tube by actuation of the handle 54. Preferably, this injection continues until the injected solution has reached the tip of the catheter 20 where, after insertion of the catheter, it interfaces with the blood in the circulatory system for a transfer of pressure signals to the transducer.

The pressure-responsive electric transducer signals are conducted by a cable 48 to a signal amplifier and other electrical or electronic measuring equipment 49.

The subject invention also extends to pressure transducer domes having one or more of the combinations of features recited above for or relative to the dome 13.

In either case, the diaphragm 19 may be retained in a circular channel 55 in the body of the dome 13, by means of solvent or adhesive bonding to the dome 13 or with the aid of an annular retainer 56 shown in FIG. 3, or by any other suitable means. In the showing of FIG. 2, the diaphragm 19 and retainer 56 have been omitted for a better visibility of the dome interior.

The exterior of the dome 13 may be provided with a thread 58 for retention by the nut 14 on the transducer body 12.

It should be recognized that the utility of the methods and apparatus herein disclosed is not limited to the blood pressure transducer field but extends to other solution or liquid handling equipment. Moreover, the utility of the invention extends also to arts in which a pressure signal is transduced relative to a liquid.

In these cases the removal and resultant lack of air or gas bubbles improves the transfer of a pressure signal from the liquid to a transducer, as well as the transfer of a pressure signal into the liquid from a pressure signal generating device.

Depending on the nature of the liquid applied through the inlet 23, the solution or liquid 34 may be of the same type or identical to that applied liquid.

The subject disclosure will suggest or render apparent various modifications or variations within the spirit and scope of the invention to those skilled in the art.

I claim:

1. In a method of keeping gas bubbles out of a circulatory system of a living organism connected via a catheter insertible into said circulatory system to a recipient device having a circular cavity connected to said catheter and tending to retain gas bubbles, the improvements comprising in combination the steps of:

provinding at said circular cavity an opening for injection of said compatible solution;

providing in said circular cavity a pocket communicating with said opening;

injecting said compatible solution through said opening into said pocket in said circular cavity;

forming a undirectional jet of said injected solution by blocking flow of said injected solution at a closed end of said pocket, thereby forming a pressure head in said pocket, and by ejecting said injected solution through an outlet of said pocket;

sweeping said ejected solution in a swirling motion along a boundary of said cavity, thereby wiping gas bubbles from said boundary; and bleeding gas from said wiped gas bubbles out of said circular cavity.

2. A method as claimed in claim 1, including the step of:

curving said pocket along part of a boundary of said circular cavity.

3. A method as claimed in claim 1, including the step of:

forming said pocket by providing in said cavity a partition being joined to a wall of said cavity at said opening and extending in spaced relationship to said wall for part thereof.

4. A method as claimed in claim 3, including the step of:

curving said partition in the manner of said circular cavity.

5. A method as claimed in claim 3 or 4, including the steps of:

providing a diaphragm across said circular cavity for deflection up to a maximum amplitude; and spacing said partition from said diaphragm to avoid contact between said partition and said diaphragm during deflection at said maximum amplitude.

6. A method as claimed in claim 1, including the steps of:

providing a duct having said opening for injection of said compatible solution;

arranging said duct at right angles to a periphery of said circular cavity; and disposing said pocket along part of said periphery.

7. A method as claimed in claim 1, including the steps of:

forming said pocket as a canal having an open bottom; and at least partially closing said open bottom.

8. A method as claimed in claim 1, including the steps of:

forming said pocket as a canal having an open bottom; and disposing a diaphragm across said circular cavity and open bottom of said canal.

9. In apparatus for handling a compatible solution relative to a circulatory system of a living organism with the aid of a catheter insertible into said circulatory system, the improvement comprising in combination:

means for receiving said compatible solution having a circular cavity;

means connected to said receiving means for coupling said catheter to said circular cavity;

means connected to said receiving means for injecting said solution into said cavity through an opening; and means for imparting a swirling motion to said injected solution to wipe gas bubbles from a boundary of said cavity, said imparting means including and delimiting a pocket in said cavity for forming a unidirectional jet of said injected solution, said pocket having a closed bottom at said opening for blocking flow of said injected solution to form a pressure head in said pocket, and said pocket having an outlet at said boundary for projecting said injected compatible solution into said circular cavity in said swirling motion whereby to wipe gas bubbles from said boundary for a bleeding thereof from said cavity.

10. Apparatus as claimed in claim 9, wherein:
said pocket is curved along part of a boundary of said circular cavity.

11. Apparatus as claimed in claim 9, wherein:
said pocket is laterally delimited by a partition joined to a wall of said cavity at said opening and extending in spaced relationship to said wall for part thereof.

12. Apparatus as claimed in claim 11, wherein:
said partition is curved in the manner of said circular cavity.

13. Apparatus as claimed in claim 11 or 12, including:
a diaphragm extending across said circular cavity for deflection up to a maximum amplitude and being spaced from said partition to avoid contact between said partition and said diaphragm during deflection at said maximum amplitude.

14. Apparatus as claimed in claim 9, including:
a duct having said opening for injection of said compatible solution and extending at right angles to a periphery of said circular cavity, with said pocket extending along part of said periphery.

15. Apparatus as claimed in claim 9, including:
a canal forming said pocket and having an open bottom; and
means for at least partially closing said open bottom.

16. Apparatus as claimed in claim 15, wherein:
said means include a diaphragm extending across said circular cavity and open bottom of said canal.

17. A pressure transducer dome, comprising:
means including a cavity for receiving a liquid solution;
means connected to said cavity for injecting said solution into said cavity through an opening; and
means for imparting a swirling motion of said injected solution to wipe gas bubbles from a boundary of said cavity, said imparting means including and delimiting a pocket in said cavity for forming a unidirectional jet of said injected solution, said pocket having a closed bottom at said opening for blocking flow of said injected solution to form a pressure head in said pocket, and said pocket having an outlet at said boundary for projecting said injected compatible solution into said circular cavity in said swirling motion whereby to wipe gas bubbles from said boundary for a bleeding thereof from said cavity.

18. A transducer dome as claimed in claim 17, wherein:
said pocket is curved along part of a boundary of said circular cavity.

19. A transducer dome as claimed in claim 17, wherein:
said pocket is laterally delimited by a partition joined to a wall of said cavity at said opening and extending in spaced relationship to said wall for part thereof.

20. A transducer dome as claimed in claim 19, wherein:
said partition is curved in the manner of said circular cavity.

21. A transducer dome as claimed in claim 19 or 20, including:
a diaphragm extending across said circular cavity for deflection up to a maximum amplitude and being spaced from said partition to avoid contact between said partition and said diaphragm during deflection at said maximum amplitude.

22. A transducer dome as claimed in claim 17, including:
a duct having said opening for injection of said compatible solution and extending at right angles to a periphery of said circular cavity, with said pocket extending along part of said periphery.

23. A transducer dome as claimed in claim 17, including:
a canal forming said pocket and having an open bottom; and
means for at least partially closing said open bottom.

24. A transducer dome as claimed in claim 23, wherein:
said means include a diaphragm extending across said circular cavity and open bottom of said canal.

25. In a method of keeping gas bubbles out of a circulatory system of a living organism connected via a catheter insertible into said circulatory system to a recipient device having a circular cavity connected to said catheter and tending to retain gas bubbles and having at said circular cavity an opening for injection of said compatible solution, the improvement comprising in combination the steps of:

injecting said compatible solution through said opening into a pocket formed in said circular cavity;
forming a unidirectional jet of said injected solution by blocking flow of said injected solution at a closed end of said pocket, thereby forming a pressure head in said pocket, and by ejecting said injected solution through an outlet of said pocket;
sweeping said ejected solution in a swirling motion along a boundary of said cavity, thereby wiping gas bubbles from said boundary; and
bleeding gas from said wiped gas bubbles out of said circular cavity.

* * * * *